(12) United States Patent
Nakaichi et al.

(10) Patent No.: US 6,582,378 B1
(45) Date of Patent: Jun. 24, 2003

(54) METHOD OF MEASURING FREQUENCY SELECTIVITY, AND METHOD AND APPARATUS FOR ESTIMATING AUDITORY FILTER SHAPE BY A FREQUENCY SELECTIVITY MEASUREMENT METHOD

(75) Inventors: Takeshi Nakaichi, Tokyo (JP); Keisuke Watanuki, Tokyo (JP); Shinichi Sakamoto, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 0 days.

(21) Appl. No.: 09/671,439

(22) Filed: Sep. 27, 2000

(30) Foreign Application Priority Data

| Sep. 29, 1999 | (JP) | ............................................... 11-276448 |
| Sep. 29, 1999 | (JP) | ............................................... 11-276449 |
| Jun. 5, 2000 | (JP) | ............................................. 2000-167265 |
| Jul. 25, 2000 | (JP) | ............................................. 2000-223768 |

(51) Int. Cl.$^7$ ................................................. A61B 5/00
(52) U.S. Cl. ................................................ 600/559
(58) Field of Search ................................ 600/559, 300, 600/23, 27, 28; 704/228; 340/384 E, 384.5, 392.3, 521; 381/56, 86, 73.1

(56) References Cited

U.S. PATENT DOCUMENTS

| 4,768,022 A | * | 8/1988 | Patterson ................. 340/384 E |
| 5,794,188 A | * | 8/1998 | Hollier ....................... 704/228 |
| 6,109,107 A | * | 8/2000 | Wright et al. ............... 600/559 |

FOREIGN PATENT DOCUMENTS

JP    2723780    3/1998

OTHER PUBLICATIONS

Patterson, Roy D., "Auditory Filter Shapes Derived with Noise Stimuli", Journal of the Acoustical Society of America, vol. 59, No. 3, pp. 640–654.*

* cited by examiner

Primary Examiner—Max F. Hindenburg
Assistant Examiner—Brian Szmal
(74) Attorney, Agent, or Firm—Carrier Blackman & Associates, P.C.; Joseph P. Carrier; William D. Blackman

(57) ABSTRACT

A method of estimating the shape of an auditory filter by finding a coefficient p of a roex (p, r) filter used as a model of the shape of the auditory filter, comprises the steps of determining the threshold masking level $N_x$ based on a tone S which adds the given value x to the threshold of hearing T of a subject in a frequency f, generating a tone S' which deducts the given value a from the tone S, generating a masker M of a center frequency f of a notch, notch width g and level $N_x$, transmitting to the subject an inspection sound which superposes the masker M on the tone S' by selsctively varying the notch width g, determining the notch width g at which the subject can perceive the tone S' to be the minimum notch width $g_{x-a}$ of the subject, calculating the coefficient p from the minimum notch width $g_{x-a}$ and the given value a, and estimating the shape of the auditory filter from the coefficient p and the given value x corresponding to the coefficient r.

20 Claims, 10 Drawing Sheets

METHOD OF MEASURING FREQUENCY SELECTIVITY, AND METHOD AND APPARATUS FOR ESTIMATING AUDITORY FILTER SHAPE BY A FREQUENCY SELECTIVITY MEASUREMENT METHOD

BACKGROUND OF THE INVENTION

1. Field of the Invention

The present invention relates to a method of measuring frequency selectivity of the sense of hearing, and a method of, and an apparatus for, estimating the shape of a human auditory filter by the frequency selectivity measurement method.

2. Description of the Relevant Art

Hearing characteristic tests for hearing impairment that are most frequently conducted nowadays are a hearing test (measurement of audiogram) and a speech intelligibility test. In the hearing test, it is possible to ascertain frequency characteristics of the threshold of hearing of the hearing impairment. In the speech intelligibility test, it is possible to determine any ability of discrimination of speech by the hearing impairment.

However, the hearing characteristics of the hearing impairment vary with individuals. It is therefore considered that these two methods can only grasp a part of the complicated hearing characteristics.

It is generally said that the shape of audiogram and ability of discrimination of speech has not only deteriorated, but their frequency selectivity has deteriorated in impaired ears. The frequency selectivity is the capability of perceiving two sounds that are different in frequency. Normal hearing can perceive two different sounds that are close in frequency, for example, 1 kHz v. 1.2 kHz, but the hearing impairment whose frequency selectivity has deteriorated cannot perceive these two different sounds.

When the extent of deterioration in the frequency selectivity becomes greater, it leads to deterioration of ability of discrimination of speech or deterioration of ability of discrimination of speech sound under noisy conditions. It is therefore very useful to know the extent of deterioration in the frequency selectivity for the hearing impairment's diagnosis, a grasp of the hearing impairment's hearing characteristics, hearing aid fittings, etc.

In recent years, an auditory filter has been suggested as a model for expressing a mechanism of frequency analysis of the human sense of hearing. This is considered to be a method for expressing a mechanism of frequency analysis of the human inner ear by band-pass filter banks. The shape of each filter (auditory filter) within these filter banks is usually measured by notched noise masking. A simplified method for measuring the frequency selectivity for the hearing impairment that uses a theory of this auditory filter is disclosed in Japanese patent No. 2723780. It is known that a roex (p, r) filter can be used as a model for the shape of a human auditory filter.

In the measurement of the auditory filter by notched noise masking, it is said that the shape of each subject's auditory filter can be measured with high accuracy. However, this measurement takes a long time and it is practically impossible to measure the shape of the auditory filter of a hearing impairment individual at any time by clinicians or audiologists. Japanese patent No. 2723780 suggests a method of measuring whether or not frequency selectivity has deteriorated in a short time. It is possible to judge whether there is any deterioration in the frequency selectivity, but is not possible to measure the extent of deterioration in the frequency selectivity, or the shape itself of the auditory filter.

The hearing threshold level of the hearing impairment naturally rises higher than that of normal hearing and if noise is superposed thereon, the threshold of detection level of a tone (probe signal) rises further. In addition, if that hearing impairment's frequency selectivity has deteriorated, the noise's influence on the individual is much greater than for normal hearing. Therefore, in many cases, the hearing impairment whose hearing level has severely deteriorated cannot detect a tone even though the tone level has reached the maximum output level of an inspection instrument (off-the-scale).

It is also said that the shape of the auditory filter varies with the level of the input signal. In the measurement of the auditory filter of normal hearing, it is said that a masker (notched noise) whose level is about 40 dB/Hz is most suitable judging from the information in the past. It is also said that when measured at a level higher than 40 dB/Hz, the shape of the auditory filter becomes broad. However, such a shape change in the auditory filter as seen in the normal hearing does not always occur in all hearing impairment cases according to their levels. There is no method of measuring the shape change characteristics of the auditory filter according to each level of the hearing impairment to date.

SUMMARY OF THE INVENTION

The primary object of the present invention is to overcome the above-mentioned drawbacks and to provide a method of measuring frequency selectivity comprising the steps of adding notched noise with a predetermined notch width to a detection sound which sets frequency and sound pressure level at a predetermined value to produce an inspection sound, transmitting the inspection sound to a subject, judging whether or not the subject can perceive the detection sound from the inspection sound by widening the notch width, and obtaining the threshold notch width for the subject.

With this method, the frequency selectivity of the hearing impairment subject whose power of hearing has highly or seriously deteriorated and whose threshold of hearing is high can also be measured by the inspection instrument without going off the scale.

Further, if the notch width is set at the threshold notch width of normal hearing, it is possible to easily judge whether the frequency selectivity of a subject has deteriorated further than that of normal hearing.

Another object of this invention is to provide a method of measuring frequency selectivity which comprises the steps of adding notched noise with a predetermined notch width to a detection sound which sets frequency and sound pressure level at a predetermined value to produce an inspection sound, transmitting the inspection sound to a subject, judging whether or not the subject can perceive the detection sound from the inspection sound by narrowing the notch width, and obtaining the threshold notch width of the subject.

With this method, the frequency selectivity of the hearing impairment subject whose power of hearing has highly or seriously deteriorated and whose threshold of hearing is high can also be measured without going off the scale of the inspection instrument.

A further object of this invention is to provide a method of measuring frequency selectivity which comprises the steps of adding noise with a predetermined notch width generated from white noise which is set at a threshold masking level, to a detection sound which sets frequency and a sound pressure level to predetermined values to produce an inspection sound, transmitting the inspection sound to a subject, judging whether or not the subject can perceive the detection sound from the inspection sound by widening a notch width, and obtaining the threshold notch width of the subject.

A further object of this invention is to provide a method of measuring frequency selectivity comprising the steps of adding noise with a predetermined notch width generated from white noise which is set to a threshold masking level to a detection sound which sets frequency and a sound pressure level at predetermined values to produce an inspection sound, transmitting the inspection sound to a subject, judging whether or not the subject can perceive the detection sound from the inspection sound by narrowing a notch width, and obtaining the threshold notch width of the subject.

With this method, it is possible to easily measure the frequency selectivity of the power of hearing.

If the sound pressure level of the detection sound is set to the threshold of hearing of the subject or to a sound pressure level which adds a predetermined level to the threshold of hearing, it is possible to easily judge whether or not the subject could detect the detection sound signal. With the hearing impairment subject whose power of hearing has highly or seriously deteriorated and whose threshold of hearing is high, it is possible to measure the frequency selectivity of the subject's sense of hearing using the inspection instrument.

Another object of this invention is to provide a method for estimating the shape of an auditory filter by finding a coefficient p of a roex (p, r) filter used as a model for the shape of the auditory filter, comprising the steps of determining a threshold masking level $N_x$ based on a tone S which adds a given value x to a threshold of hearing T of a subject in frequency f, generating a tone S' which deducts a given value a from the tone S, generating a masker M with a notch width g and a level $N_x$ including the frequency f in the notch, transmitting to a subject an inspection sound which superposes the masker M on the tone S', measuring a minimum notch width $g_{x-a}$ of the subject by changing the notch width g, calculating a coefficient p from the minimum notch width $g_{x-a}$ and the given value a, and estimating the shape of the auditory filter by the coefficient p and the given value x corresponding to a coefficient r.

With this method, it is possible to estimate the effective shape of the auditory filter to efficiently and accurately conduct a diagnosis of the hearing impairment, to obtain a grasp of the hearing characteristics of the hearing impairment, of hearing aid fittings, etc.

By using the given value x as a parameter, when the shape of the auditory filter is estimated from the coefficient p calculated from the minimum notch width $g_{x-a}$ and the value a and the value x corresponding to the coefficient r, it is possible to estimate the shape of the auditory filter corresponding to the input signal. It is also possible to know the relationship between the input signal level and the auditory filter.

A further object of this invention is to provide an apparatus for estimating the shape of an auditory filter by finding a coefficient p of a roex (p, r) filter used as a model for the shape of the auditory filter, comprising a tone generation element for generating a tone with a predetermined frequency, a tone level setting element for amplifying or attenuating the tone generated at the tone generation element to a predetermined level;

a noise generation element for generating noise without a notch, a noise level setting element for amplifying or attenuating the noise generated at the noise generation element to a predetermined level, a notch width setting element for adding a notch including frequency of the tone to the noise, a notched noise superposition element for superposing notched noise output from the notch width setting element on a tone output from the tone level setting element, an inspection sound transmission element for transmitting an inspection sound output from the notched noise superposition element to a subject, and an auditory filter calculation and indication element for calculating a coefficient p of the roex (p, r) filter based on a notch width at a point where the subject can perceive the inspection sound and for indicating the filter shape from the coefficients p and r obtained.

With this apparatus, it is possible to estimate the shape of the effective auditory filter to efficiently and accurately conduct a diagnosis of the hearing impairment, to obtain a grasp of the hearing characteristics of the hearing impairment, of hearing aid fittings, etc.

Further, when the threshold masking level $N_x$ and/or the minimum notch width $g_{x-a}$, are measured, if transmission of the tone is started at predetermined time intervals after starting transmission of the masker to the subject, it is possible to easily judge the validity of the subject's response from the timing of tone transmission and the timing of the response by the subject.

The above and other objects, features and advantages of the present invention will become more apparent from the following description when taken in conjunction with the accompanying drawings.

BRIEF DESCRIPTION THE DRAWINGS

DETAILED DESCRIPTION OF THE PREFERRED EMBODIMENTS

The preferred embodiments of the present invention will be described hereunder with reference to the accompanying drawings.

Figure 1:
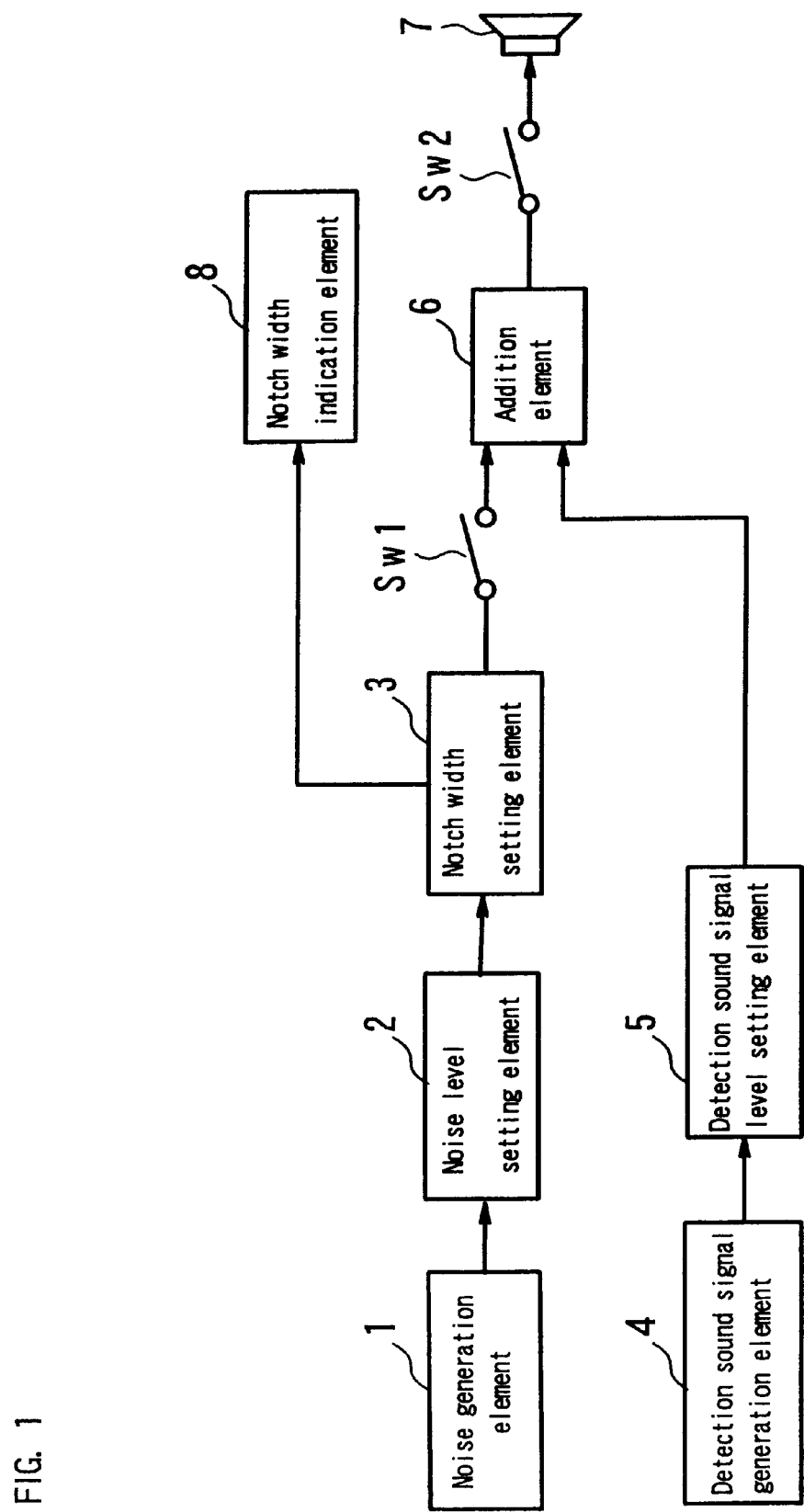
FIG. 1 is a schematic diagram of an apparatus for practicing a method of measuring frequency selectivity according to the present invention.

As shown in FIG. 1, an apparatus for practicing a method of measuring frequency selectivity according to the present invention comprises a noise generation element 1, a noise level setting element 2, a notch width setting element 3, a detection sound signal generation element 4, a detection sound signal level setting element 5, an addition element 6, a receiver 7, a notch width indication element 8, and the like.

The noise generation element 1 has a function of outputting a noise signal, for example, a white noise signal.

The noise level setting element 2 has a function of setting a level of a noise signal output from the noise generation element 1 at a calibrated level and indicating a sound pressure level output from the receiver 7. The calibrated level means the level of a signal for generating the desired sound pressure on acoustic load such as a coupler attached to the receiver 7. For example, when the calibrated level is set at an indication of Ln [dBSPL], the noise level setting element 2 outputs noise with an output level generating the sound pressure of Ln [dBSPL] per 1 [Hz] on the acoustic load.

The notch width setting element 3 has a function of adding a notch with the desired notch width whose desired frequency is center frequency to a noise signal output from the noise level setting element 2 and outputting an electric signal showing a value of the notch width at that time.

The detection sound signal generation element 4 has a function of outputting a detection sound signal, i.e. a sinusoidal wave signal with a predetermined frequency.

The detection sound signal level setting element 5 has a function of setting the detection sound signal output from the detection sound signal generation element 4 at a calibrated level and of indicating the level of sound pressure output from the receiver 7. The calibrated level means the level of a signal for generating the desired sound pressure on an acoustic load such as a coupler attached to the receiver 7. For example, when the calibrated level is set at an indication of Ld [dBSPL], the detection sound signal level setting element 5 outputs the detection sound signal with an output level generating the sound pressure of Ld [dBSPL] on the acoustic load.

The addition element 6 has a function of adding (superposing) a noise signal output from the notch width setting element 3 to a sinusoidal wave signal (detection sound signal) output from the detection sound level setting element 5 to produce an inspection sound signal.

The receiver 7 has a function of electroacoustically transducing an electric signal (inspection signal) output from the addition element 6 and of outputting an acoustic signal based on the electric signal as the inspection sound.

The notch width indication element 8 has a function of indicating notch width based on the electric signal in response to the notch width output from the notch width setting element 3.

Figure 2:
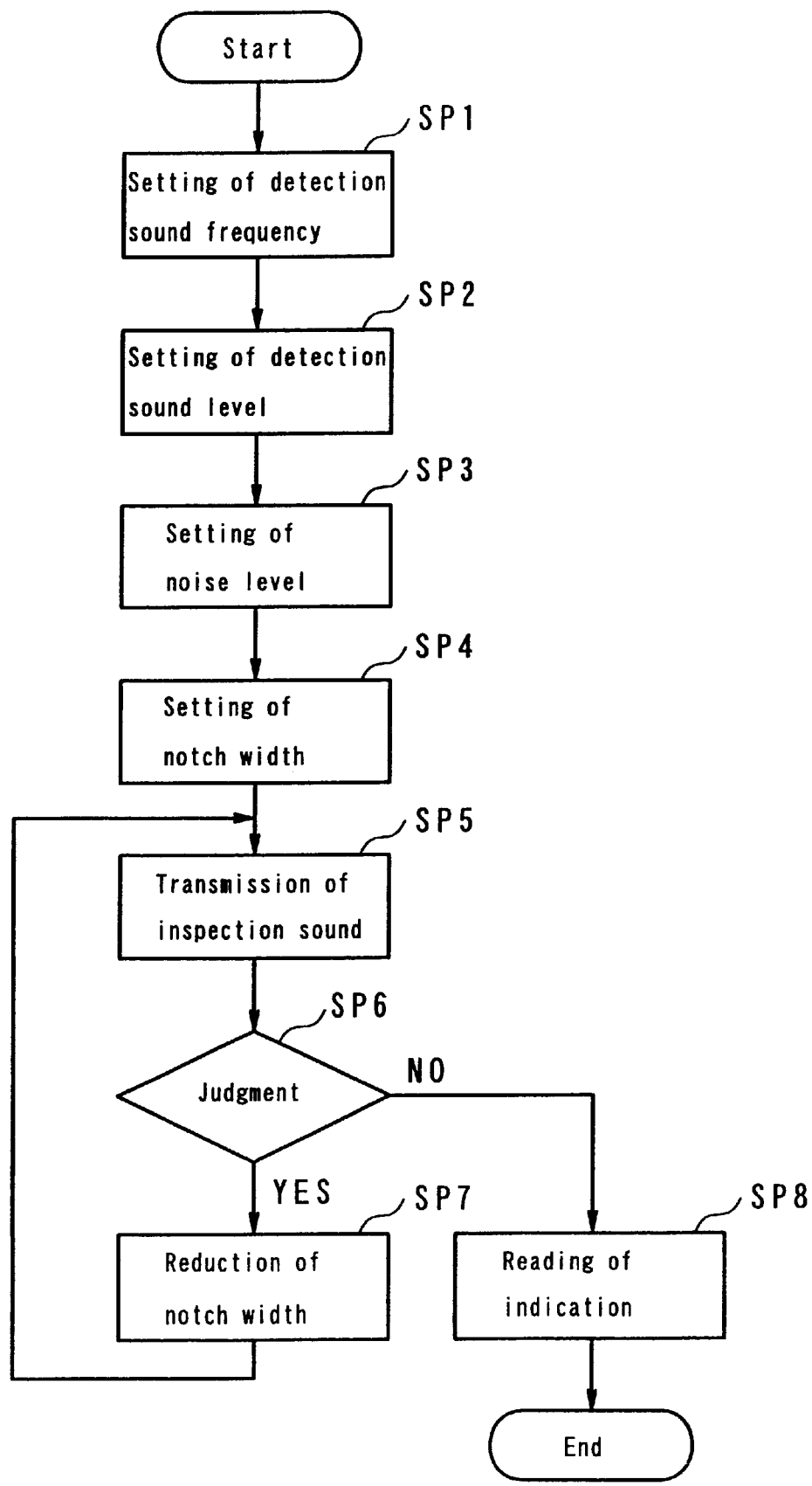
FIG. 2 is a flow chart of a first embodiment of the method of measuring frequency selectivity according to the present invention.

A first embodiment of a method of measuring frequency selectivity by the above-mentioned apparatus for measuring the frequency selectivity according to the present invention will now be described with reference to a flow chart as shown in FIG. 2.

First, in step SP 1, an operator operates the detection sound signal generation element 4 to set the frequency of the detection sound signal output from the detection sound signal generation element 4 at a frequency f whose frequency selectivity is to be measured. In this case, a switch Sw 1 (see FIG. 1) is switched OFF to prevent noise signal output from the notch width setting element 3 from entering the addition element 6. A switch Sw 2 (see FIG. 1) is also switched OFF to prevent noise caused by regulation from being output from the receiver 7.

Then, in step SP 2, the operator regulates the output of the detection sound signal level setting element 5 to a small value in advance so as to set the sound pressure of the detection sound output from the receiver 7 to the threshold of hearing T [dBSPL]. Then, the switch Sw 2 is switched ON to transmit the detection sound to a subject.

When the subject indicates that the detection sound is inaudible, the operator operates the detection sound signal level setting element 5 to slightly raise the detection sound signal level and transmits the detection sound again to the subject. This operation is repeated until a signal indicating that the detection sound is audible is received from the subject. This step SP 2 is completed when the signal that the detection sound is audible is given.

When the step SP 2 is completed, the level of the detection sound signal output from the detection sound signal level setting element 5 has been set to the threshold of hearing T [dBSPL] of the subject.

Now, in step SP 3, after the switch Sw 1 is switched ON, the noise level setting element 2 is operated to set x [dBSPL] per 1 Hz of the noise output from the noise level setting element 2. The relationship is x=T [dBSPL]. T is the level of the detection sound signal obtained in step SP 2.

Next, in step SP 4, the notch width setting element 3 is operated to set the notch width g of noise output from the notch width setting element 3 at a predetermined value. The notch width g is shown by the relationship g=Δf/fc. Δf is the frequency from noise to the inspection sound. Also, fc is the center frequency of the notch and adapted to agree with the frequency f of the detection sound signal generation element 4. The notch width g is set at 2.

Figure 3:
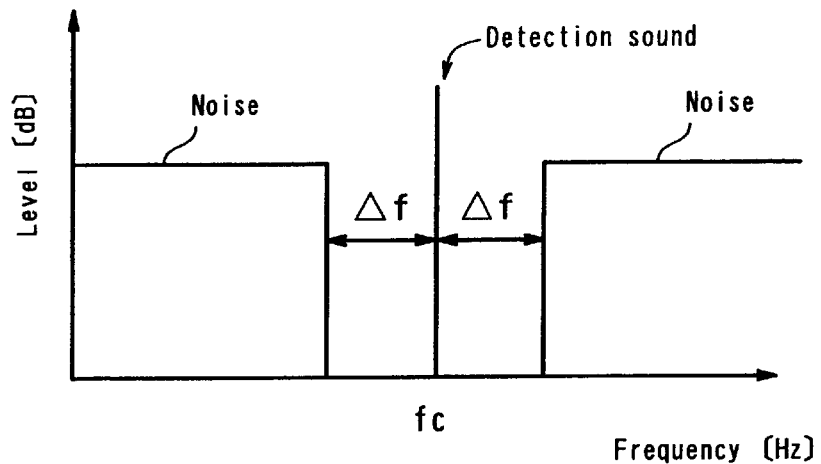
FIG. 3 is a conceptual view of an inspection sound used in the method of measuring frequency selectivity.

The detection sound signals obtained by the steps of SP 1 through SP 3, i.e. the frequency spectrum of the output signal (detection sound signal+noise signal) of the addition element 6 is shown in FIG. 3.

Next, in step SP 5, the detection sound is transmitted to the subject. Namely, by switching the switch Sw 2 ON, the inspection sound signal output from the addition element 6 is electroacoustically transduced by the receiver 7 and the inspection sound based on the inspection sound signal is transmitted to the subject.

In step SP 6, it is determined whether or not the subject could perceive the detection sound in the inspection sound. Namely, the operator asks the subject whether or not the detection sound in the inspection sound is audible. At the point where the subject perceives that the detection sound is included in the inspection sound, the program goes to step SP 7 and then step SP 5 in turn.

In step SP 7, the operator resets the notch width g to a slightly smaller value. Namely, Δf is set to a slightly smaller value. The steps SP 5, SP 6 and SP 7 are repeated until the subject cannot perceive that the detection sound is included in the inspection sound. Namely, a marginal notch width (the threshold notch width g') where the subject can perceive the detection sound in the inspection sound is sought based on a method of limits.

In step SP 6, when the subject cannot perceive that the detection sound is included in the inspection sound, the program goes to step SP 8, wherein the operator reads the threshold notch width g' indicated by the notch width indication element 8. Thus, the measurement of frequency selectivity is completed.

Figure 5:
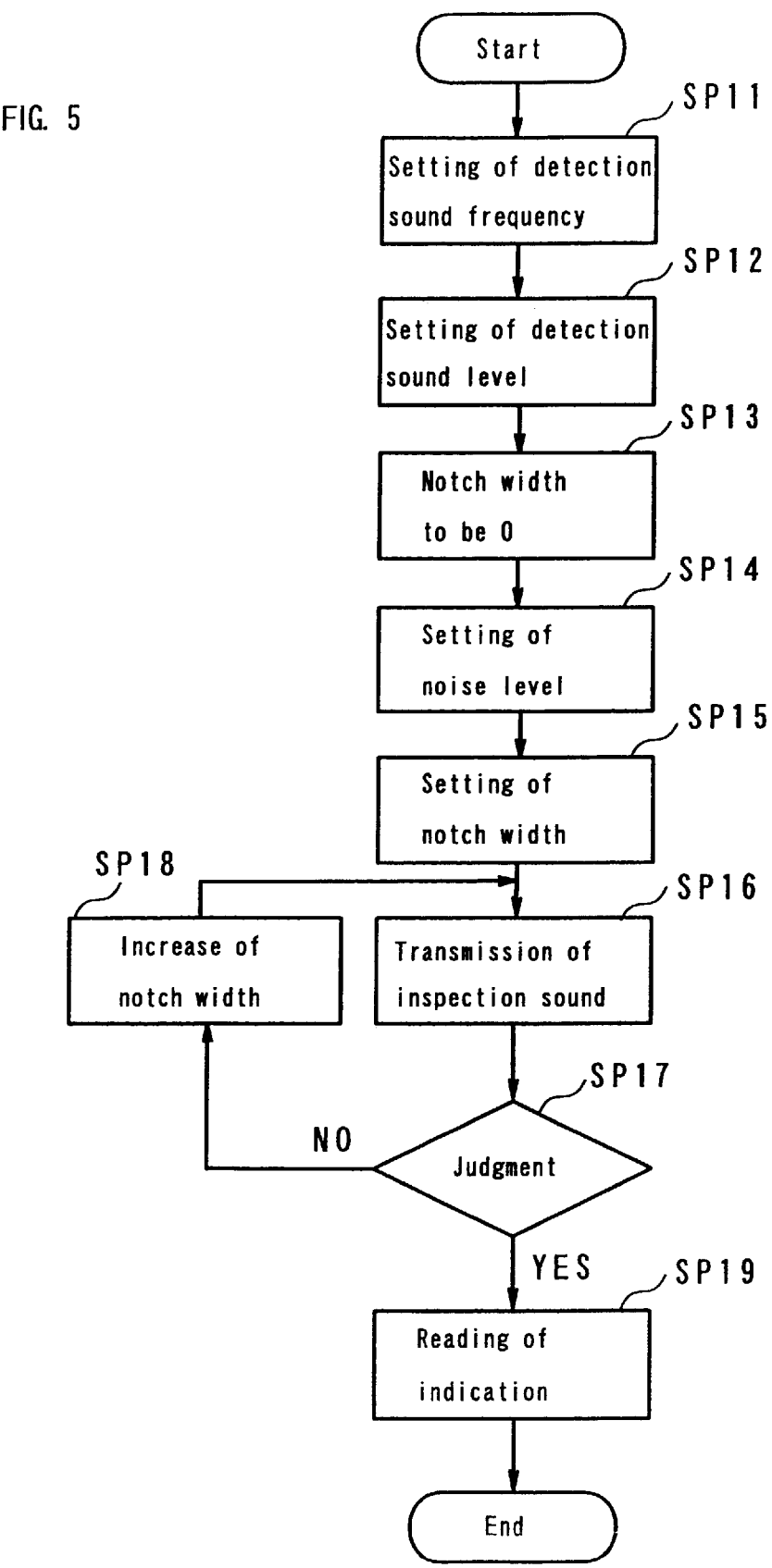
FIG. 5 is a flow chart of a second embodiment of a method of measuring frequency selectivity according to the present invention.

A second embodiment of a method of measuring frequency selectivity according to the present invention will now be described with reference to a flow chart as shown in FIG. 5.

First, in step SP 11, the operator operates the detection sound signal generation element 4 so as to set the frequency of the detection sound signal output from the detection sound signal generation element 4 at the frequency f whose frequency selectivity is to be measured. In this case, the switch Sw 1 is switched OFF to prevent the noise signal output from the notch width setting element 3 from entering the addition element 6. The switch Sw 2 is also switched OFF to prevent the noise caused by regulation from being output from the receiver 7.

Then, in step SP 12, the operator operates the detection sound signal level setting element 5 so as to set the sound pressure of the detection sound output from the receiver 7 at the threshold of hearing T [dBSPL] of the subject.

In this embodiment, the so-called method of limits is used to set the sound pressure of the detection sound at the threshold of hearing of the subject. Namely, the detection sound signal level setting element 5 is operated first to regulate the output of the detection sound signal level setting element 5 to a sufficiently small value. Then, the switch Sw 2 is switched ON to transmit the detection sound to the subject.

When the subject signals the operator to the effect that the detection sound at that time is inaudible, the operator operates the detection sound signal level setting element 5 to slightly raise the detection sound signal level and transmit again the detection sound to the subject. This operation is repeated until the subject acknowledges perception of the detection sound. This step SP 12 is completed when the operator receives the signal that the subject can perceive the sound.

When step SP 12 is completed, the detection sound signal level output from the detection sound signal level setting element 5 has been set to the threshold of hearing T [dBSPL] of the subject.

Next, in step SP 13, the notch width setting element 3 is operated to set the notch width of notched noise output from the noise level setting element 2 at 0. With this setting, the notch width setting element 3 is adapted to output a white noise signal.

Then, in step SP 14, the level of the white noise signal output from the noise level setting element 2 is set at the threshold masking level. When a sound that adds white noise to the detection sound is sent to the subject, the threshold level at which the subject can perceive the detection sound is called the threshold masking level.

In this embodiment, the method of limits is used to set the threshold masking level. First, the noise level setting element 2 is operated to sufficiently reduce the level of the white noise signal output from the noise level setting element 2. Then, the switches Sw 1 and Sw 2 are switched ON to transmit the sound that adds the detection sound to the white noise, to the subject. The noise level setting element 2 is operated to raise the level of the white noise signal until the subject cannot perceive the detection sound from the sound that adds the detection sound to the white noise.

Next, in step SP 15, the notch width setting element 3 is operated to apply the predetermined notch width, for example, the notch with a notch width g=0.05 to the white noise signal output from the notch width setting element 3 to produce noise. The notch width g is shown here in the relationship g=Δf/fc. However, Δf is the frequency from noise to the inspection sound. Also, fc is the center frequency of the notch and adapted to agree with the frequency f of the detection sound signal generation element 4 set in step SP 11.

The inspection sound signal obtained from the steps of SP 11 through SP 15, i.e. frequency spectrum of output signal (detection sound signal+noise signal) of the addition element 6 is shown in FIG. 3.

Then, in step SP 16, the inspection sound signal output from the addition element 6 is electroacoustically transduced by the receiver 7 and the inspection sound based on the inspection sound signal is transmitted to the subject.

In step SP 17, it is determined whether or not the subject can perceive the detection sound in the inspection sound. Namely, the operator asks if the subject can perceive the detection sound in the inspection sound. When the subject cannot perceive that the detection sound is included in the inspection sound, the program goes to step SP 18, wherein the notch width g is widened by the predetermined width.

Next, the program again goes to step SP 16, wherein the inspection sound is transmitted to the subject. Thus, the process of the steps SP 18, SP 16 and SP 17 is repeated until the subject can perceive that the detection sound is included in the inspection sound. Namely, a marginal notch width (the threshold notch width g') at which the subject can perceive the detection sound in the inspection sound is sought based on the method of limits.

In step SP 17, when the subject can perceive the detection sound in the inspection sound, the program goes to step SP 19, wherein the operator reads the threshold notch width g' indicated at the notch width indication element 8 and records the value if necessary. Thus, the measurement of frequency selectivity is completed.

Figure 4:
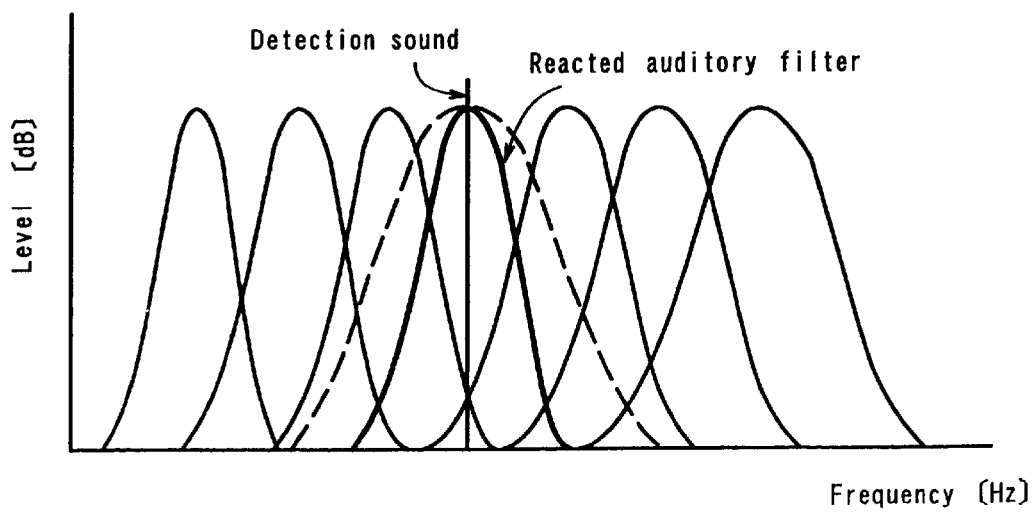
FIG. 4 is a physical model view showing frequency selectivity of the human sense of hearing.

As a physical model indicating frequency selectivity of a human sense of hearing, a filter bank with a special characteristic as shown in FIG. 4, i.e. a filter unit constituting a band-pass filter bank by combining a plurality of narrow-band-pass filters is suggested. In FIG. 4, the narrow-band-pass filter of which the base is wide (a dotted line) shows an auditory model of a person whose frequency selectivity has deteriorated. On the other hand, the narrow-band-pass filter of which the base is narrow (a solid line) shows an auditory model of a person with normal frequency selectivity. A thick solid line shows the reacted auditory filter.

The threshold notch width g' obtained in the step of SP 8 or SP 19 shows the extent of the base of the narrow-band-pass filter which constitutes a human sense of hearing of which the center frequency is f, i.e. it is considered that the threshold notch width g' shows the frequency selectivity of the sense of hearing in the measured frequency f. When the value of the threshold notch width g' is large, it means that the base of the narrow-band-pass filter is wide, and when the value is small, the base is not wide. According to the tests, it is confirmed that the threshold notch width g' shows the frequency selectivity of the sense of hearing with considerable accuracy.

In the step of SP 2 or SP 12 according to the embodiments stated above, the level T [dBSPL] corresponding to the threshold of hearing of the subject is used as a level x [dBSPL] of the detection sound, but the present invention is not to be so limited. It is apparent that the level of the detection sound may be raised slightly higher than that corresponding to the threshold of hearing of the subject, for example, to have the relationship x=T+5 [dBSPL].

When the detection sound level is set to the threshold of hearing of the subject to effect the measurement, the detection sound signal level becomes a detection threshold level. Therefore, there is some possibility that it is very difficult to judge whether or not the subject can perceive the detection sound in the inspection sound. Since the level of the detection sound is raised slightly higher than that corresponding to the threshold of hearing of the subject, the subject can easily perceive the detection sound in the inspection sound.

Also, in step SP 3 of the above-mentioned embodiments, it has been explained that the noise level setting element 2 is operated to set the noise level y output from the noise level setting element 2 at y=x [dBSPL]. However, the noise level may be slightly raised or lowered, for example, to have the relationship y=x+5 [dBSPL].

In the embodiments stated above, it has been explained that frequency of the detection sound signal output from the detection sound signal generation element 4 is arranged to agree with the center frequency of notched noise set by the notch width setting element 3 (f=fc). However, it is not always necessary that they agree with one other, but it is enough if the detection sound signal is included in the notch width.

Further, in the above-mentioned embodiments, when the threshold notch width g' of the subject is sought, the following steps have been explained. The notch width g of notched noise is first set narrower and the detection sound is transmitted to the subject. When the subject cannot perceive the detection sound from the inspection sound, the notch width g of the notched noise is gradually widened and the inspection sound is transmitted again to the subject.

However, since it is one of the objects of the present invention to find the threshold notch width g', the following steps may be taken. First, the notch width g of the notched noise is set wider and the inspection sound is transmitted. When the subject can perceive the detection sound from the inspection sound, the notch width g of notched noise can be gradually narrowed.

In the embodiments above, in step SP 4, the notch width g was set to 2 at the start of the measurement, but the present invention is not to be so limited. It is apparent that the value of the notch width g at the start of measurement can be set to an average notch width (standard notch width) so that the value can be gradually increased. With this arrangement, it is possible to easily judge whether or not the frequency selectivity of the subject has deteriorated more than that of normal hearing.

Further, in the above-mentioned embodiments, in setting the detection sound level (steps SP 2 and SP 12) and setting the threshold masking level (step SP 14), a method of limits is used. However, it is also possible to use a psychophysical measurement method such as two alternative forced choices for selecting either the inspection sound to which the detection sound was added or the inspection sound to which the detection sound was not added for the level setting.

In the embodiments stated above, the method of limits is used to find the threshold notch width g', but the psychophysical measurement method such as the two alternative forced choices may be used instead.

Figure 6:
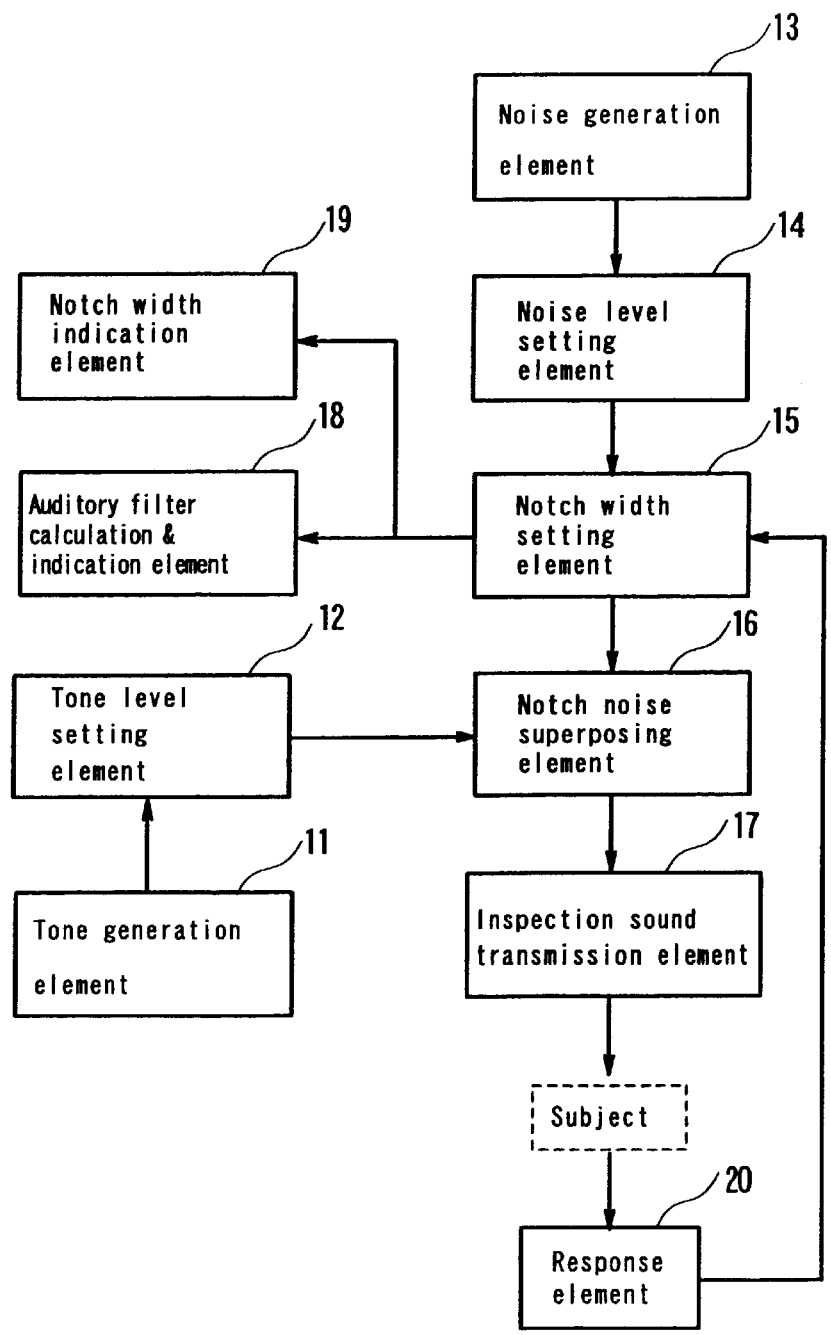
FIG. 6 is a schematic diagram of an apparatus for estimating the shape of an auditory filter according to the present invention.

Referring to FIG. 6, an apparatus for estimating the shape of an auditory filter according to the present invention is provided which comprises a tone generation element 11, a tone level setting element 12, a noise generation element 13, a noise level setting element 14, a notch width setting element 15, a notched noise superposing element 16, an inspection sound transmission element 17, an auditory filter calculation and indication element 18, a notch width indication element 19, a response element 20 and the like.

The tone generation element 11 outputs a sinusoidal wave signal of a predetermined frequency f as a tone (pure tone). A value of the frequency f can be set voluntarily. The tone generation element 11 may be constituted by a CPU to generate the tone by a predetermined program, or constituted by a memory to store a tone signal in advance.

The tone level setting element 12 amplifies or attenuates the tone generated at the tone generation element 11 to a predetermined level. The tone level setting element 12 outputs a tone of the threshold of hearing T [dBSPL] of a certain subject, a tone S of level T+x [dBSPL] which adds the given value x [dB] to the threshold of hearing T [dBSPL], a tone S' of level T+x−a [dBSPL] which deducts the given value a [dB] from level T+x [dBSPL], etc. The relation is x>a.

The noise generation element 13 outputs noise without a notch (white noise etc.). The noise generation element may be constituted by a CPU to generate noise by a predetermined program, or constituted by a memory to store a noise signal in advance.

The noise level setting element 14 amplifies or attenuates the noise generated at the noise generation element 13 to a predetermined level. The noise level setting element 14 outputs noise of a level (the threshold masking level) $N_x$ which can mask the tone S of a level T+x [dBSPL], etc.

The notch width setting element 15 gives a notch whose center frequency $f_c$ is the same ($f_c$=f) as the frequency f of the tone to the noise output from the noise level setting element 14. The notch width g of this notch is varied at any time by the response from the subject. The notch with setting element 15 may be constituted as such a filter that can realize the desired notch, or a plurality of notched noises may be stored in memory in advance so that noise having various notches can be selectively used at any time.

The notched noise superposing element 16 superposes the center frequency $f_c$, notch width g and notched noise (masker M) of level $N_x$ output from the notch width setting element 15 on a tone S' output from the tone level setting element 12 to provide the inspection sound.

The inspection sound transmission element 17 transmits the inspection sound output from the notched noise superposing element 16 to a subject. The subject listens to the inspection sound and responds on perception of the tone S'.

The auditory filter calculation and indication element 18 calculates a filter coefficient p of the roex (p, r) filter based on the notch width g when the subject can perceive the tone S' and indicates the filter shape from the filter coefficients p and r obtained.

The roex (p, r) filter is defined by the following formula (1).

$$w(g)=(1-r)(1+pg)e^{-pg}+r \tag{1}$$

Now, p is a coefficient corresponding to a band width (angle of slope) of a filter, r is a coefficient corresponding to a dynamic range of the filter and g is the notch width (=Δf/fc). To show the auditory filter as the formula (1), notched noise masking data Ps (g) obtained from the notched noise masking is used. This is defined by the following formula (2).

$$Ps(g) = 2Kf_c N_x \int_g^{g\;max} w(h)\,dh \qquad (2)$$

Here, $g_{max}$ is an upper limit of the notch width g, K is sensitivity of each person and $N_x$ is a level of the masker M per 1 [Hz].

The notch width indication element 19 indicates the notch width g of the masker M output from the notch width setting element 15.

The response element 20 outputs a countersign when the subject can perceive the tone S' from the inspection sound transmitted from the inspection sound transmission element 17 by the operation of the subject and a countersign when the subject cannot perceive the tone S'. The countersign when the subject cannot perceive the tone S' is output to the notch width setting element 15.

As will be understood, it is possible to use only the countersign when the subject can perceive the tone S'. When the countersign is not output by the subject in the case where the subject can should have been able to perceive it for the predetermined time is not output, it can be considered that the subject could not perceive the tone S' and the program may go to the next step.

An operation of the apparatus for estimating the shape of the auditory filter as constituted above will now be explained hereunder.

The masker M is superposed on the tone S' in the notched noise superposing element 16 to produce the inspection sound. The produced inspection sound is transmitted to the subject through the inspection sound transmission element 17.

The subject listens to the inspection sound and responds using the response element 20 to acknowledge perception of the tone S'.

Figure 7:
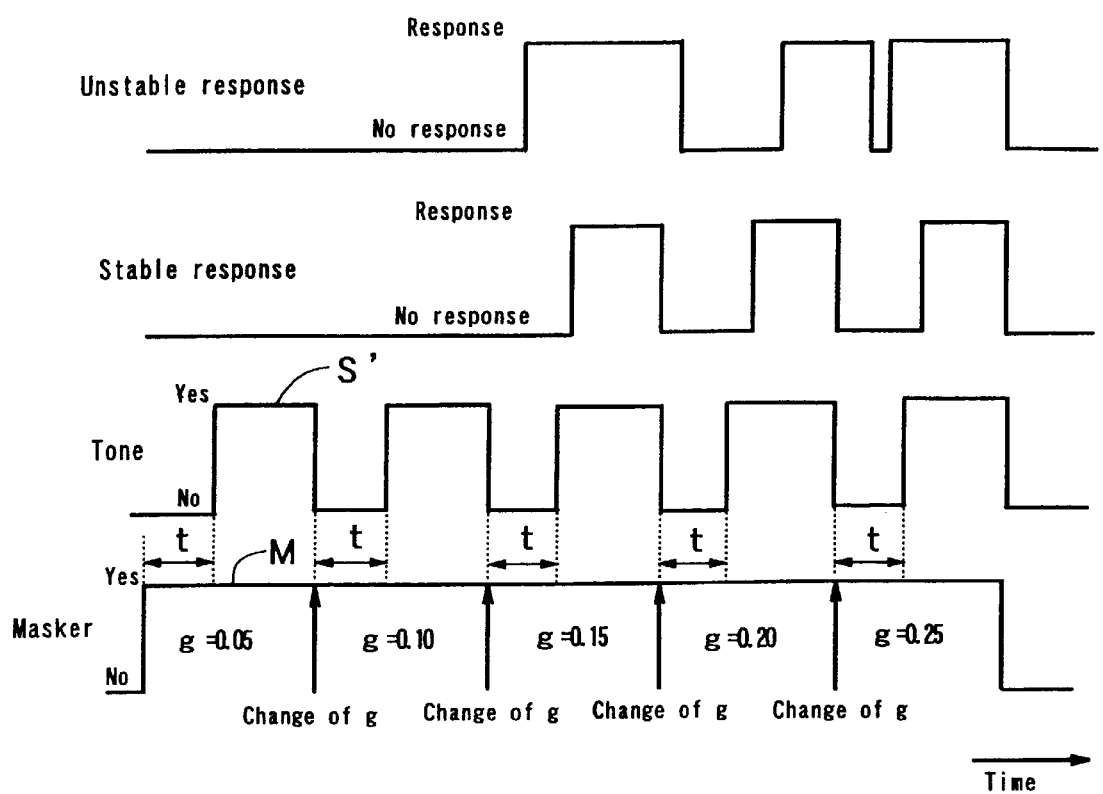
FIG. 7 is a timing chart showing the relationship between transmission of an inspection sound and a response by a subject.

As shown in FIG. 7, when the first inspection sound is transmitted to the subject, it is possible to set the level of the tone S' output from the tone level setting element 12 at 0 by the predetermined time t at the start of transmission of the inspection sound. (Transmission of the tone S' can be delayed by the predetermined time t relative to the masker M).

In the notch width setting element 15, a new masker M is provided according to the response, and output again to the notched noise superposing element 16. Thus, the notch width g of the masker M may be automatically altered according to the response by the subject (it may be constituted by a CPU to prepare the exclusive program), or a measurer can issue a manual instruction each time this happens.

Even when a new inspection sound is transmitted to the subject after the notch width g is increased, it is also possible to set the level of the tone S' output from the tone level setting element 12 to 0 by the predetermined time t at the start of transmission of the new inspection sound. (The transmission of the tone S' can be delayed by the predetermined time t relative to the masker M).

The notch width g during measurement is indicated in the notch width indication element 19. By gradually increasing the notch width g, the minimum notch width (the threshold notch width) $g_{x-a}$ where the subject can perceive the tone S' is measured. In the auditory filter calculation and indication element 18, a filter coefficient p of the roex (p, r) filter is calculated based on the measured notch width $g_{x-a}$ and the set value a as shown below. The filter shape is indicated from the filter coefficient p and the value x corresponding to the filter coefficient r.

Figure 8:
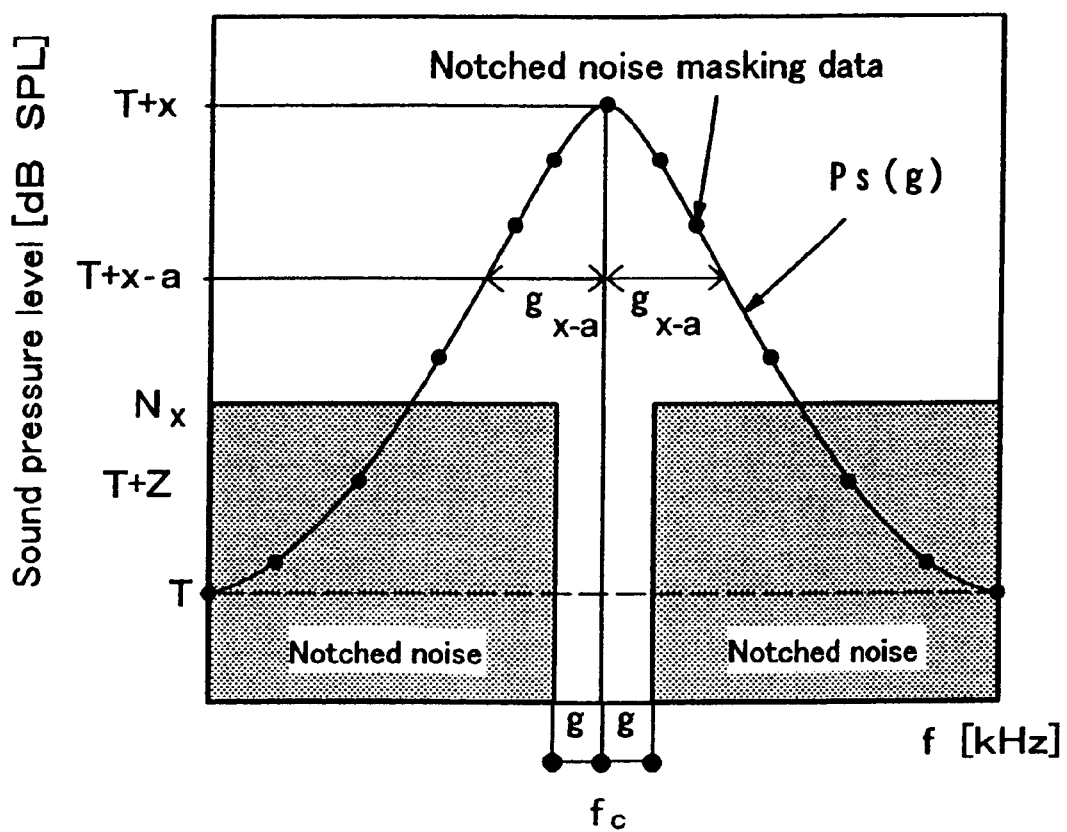
FIG. 8 is an explanatory view of a method of estimating the shape of an auditory filter according to the present invention.

As shown in FIG. 8, $g_{x-a}$ is equivalent to the band width at a point attenuated by a [dB] from the top in the notched noise masking data characteristics. In the formula (2), if r is sufficiently small and $g_{max}$ has, for example, a value of about 0.8, the following formula (3) is available.

$$Ps(0)/Ps(g_{x-a}) \approx \frac{2e^{p \cdot g_{x-a}}}{2 + p \cdot g_{x-a}} \qquad (3)$$

Base on the relationship a [dB]≈10 log (Ps(0)/Ps (g x–a), the following formula (4) is available.

$$a[\mathrm{dB}] \approx 10\,\log\!\left\{\frac{2e^{p \cdot g_{x-a}}}{2 + p \cdot g_{x-a}}\right\} \qquad (4)$$

When the value of a, and $g_{x-a}$ found by the measurement are substituted in the above formula (4), it is possible to get the estimated value of the filter coefficient p.

Figure 10:
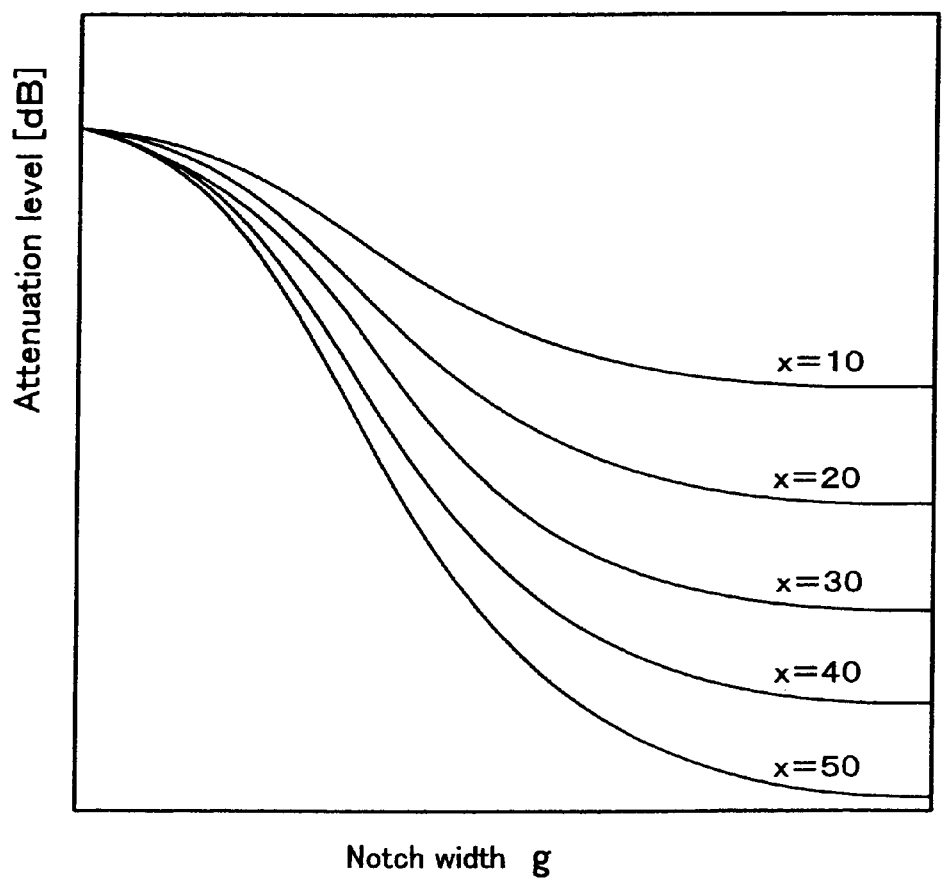
FIG. 10 is a view showing the shape of an auditory filter determined according to the present invention.

Thus, by setting the value x corresponding to the filter coefficient r at, for example, 10, 20, 30, 40 and 50 [dB] respectively, the estimated value of the filter coefficient p is found for each of them. In FIG. 10, the shape of the auditory filter is shown in the parameter of the value x [the notch width g in the abscissa; attenuation level in the ordinate].

Figure 9:
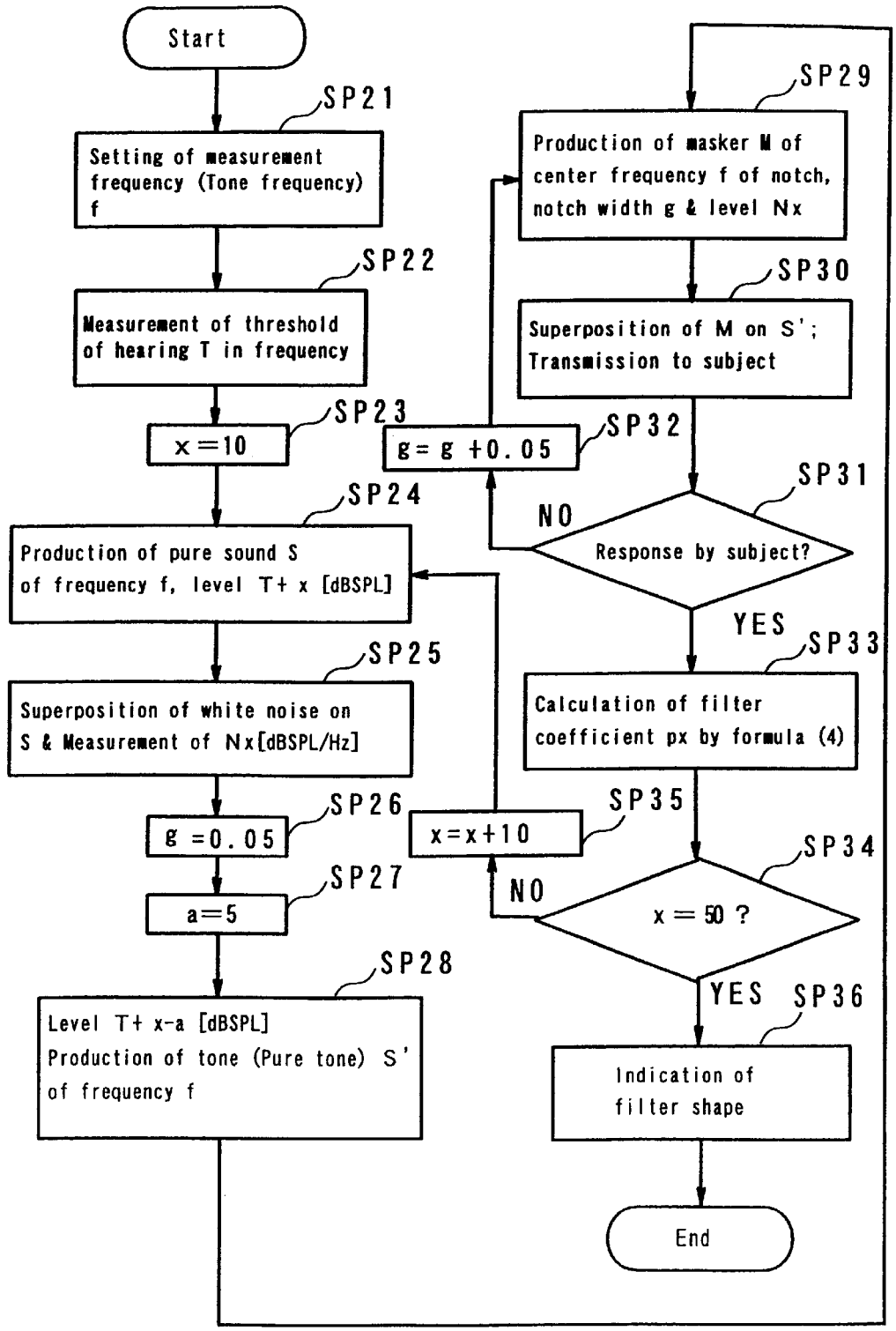
FIG. 9 is a flow chart showing the steps of a method of estimating the shape of an auditory filter according to the present invention.

Next, a method of estimating the shape of the auditory filter according to the present invention will now be explained with reference to a flow chart of FIG. 9.

First, in step SP 21, frequency to be measured (tone frequency) f is set and in step SP 22, the pure-tone threshold of hearing T [dBSPL] in frequency f is measured in a condition without superposing noise.

Then, in step SP 23, a value of coefficient x for determining a dynamic range of the notched noise masking data is set. The relationship is x=10. In step SP 24, the pure tone (tone) S of frequency f [Hz] and level T+x [dBSPL] is provided.

In step SP 25, the white noise whose level is sufficiently small is superposed on the tone S and the minimum level (the threshold masking level) $N_x$ [dBSPL/Hz] where the subject cannot perceive the tone S is measured by gradually raising the white noise level.

In step SP 26, the notch width g of noise of the level $N_x$ [dBSPL/Hz] is set at a predetermined value. The relationship is g=0.05. In step SP 27, the value a [dB] which is deducted from level T+x [dBSPL] of the tone S is set at a predetermined value (x>a). The relationship is a=5.

In step SP 28, the pure tone (tone) S' of frequency f [Hz] and level T+x–a [dBSPL] is provided. In step SP 29, the masker M of the center frequency of notch $f_c(=f)$, notch width g and level $N_x$ [dBSPL/Hz] is provided.

Then, in step SP 30, the masker M is superposed on the tone S' and is transmitted to the subject as the inspection sound. Also, in step SP 31, the subject is required to judge whether or not the tone S' is perceptible from the inspection sound. If the subject does not acknowledge perception of the tone S', the program goes to step SP 32 to increase the value of the notch width g (an increment is 0.05). The steps 29 to 31 are repeated until the subject acknowledges perception of the tone S'.

As shown in FIG. 7, when the inspection sound is transmitted to the subject it is possible to set the initial level of the tone S' output from the tone level setting element 12 to 0 by the predetermined time t at the start of transmission of the inspection sound. (Transmission of the tone S' can be delayed longer by the predetermined time t relative to the masker M). In this manner, when a new inspection sound is transmitted to the subject after increasing the notch width g at step SP 32, it is also possible to set the level of the tone S' output from the tone level setting element 12 at 0 by the predetermined time t at the starting time of transmission of the new inspection sound.

When the timing of the start of transmission of the tone S' is remarkably different from the timing of the response, it is possible to repeat the measurement under the same conditions as before until a stable response is received. Also, the predetermined time t need not be a constant value, but can be changed at random at each measurement.

Thus, by delaying the transmission of the tone S' by a predetermined time t relative to the masker M at the time of transmission of the first inspection sound and by stopping the transmission of the tone S' for a while when the value of the notch width g of the masker M is altered and transmitting the tone S' to the subject after an elapse of the predetermined time t, it is possible to judge the validity of the response by the subject if the timing of the response by the subject is observed.

As shown in FIG. 7, if there is a response indicating that the subject can perceive the tone S' after it is transmitted and there is no response indicating that the subject perceives the tone S' when the transmission of the tone S' is stopped, the response by the subject is considered normal or stable. On the other hand, if there is a response indicating that the subject can perceive the Tone S' before the tone S' is transmitted to the subject and/or the response indicating that the subject perceives the tone S' is maintained even after the transmission, of the tone S' is stopped, the response by the subject is considered abnormal unstable. In this case, the measurement can be conducted again or the setting of the level of the tone S' and/or the level of the masker M may be changed.

In step SP 31, when the response indicating that the subject can perceive the tone S' is given, the notch width g at that time is determined to be the minimum notch width $g_{x-a}$ of the subject. In step SP 33, the estimated value of the filter coefficient $p_x$ (x=10) of the roex (p, r) filter is calculated by the formula (4).

Then, in step SP 34, it is judged whether or not x is equal to 50 (x=50). If x is not equal to 50, the program goes to step SP 35 to obtain the relationship x=x+10. The steps 24 to 33 are repeated until x=50 is obtained and the estimated value of the filter coefficient $p_x$ for a new x (x=20, 30, 40 or 50) is calculated by the formula (4). An increment of x is 10 and measurements up to x=50 are conducted.

When it is judged that x is equal to 50 (x=50) in step SP 34, the program goes to step SP 36. As shown in FIG. 10, the shape of auditory filter having the parameter of the value x (x=10, 20, 30, 40, 50) is indicated (the notch width g as abscissa; the attenuation level as ordinate).

Figure 11A:
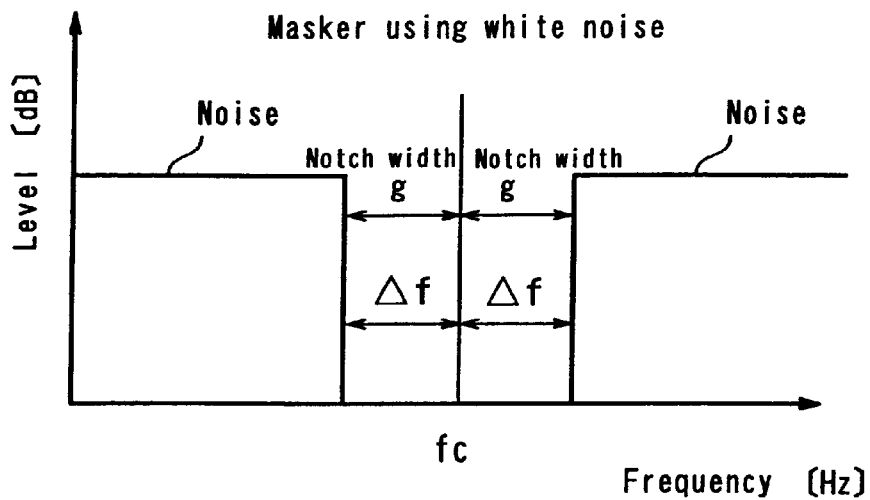
FIGS. 11(a) and 11(b) are schematic diagram of a masker.
Figure 11B:
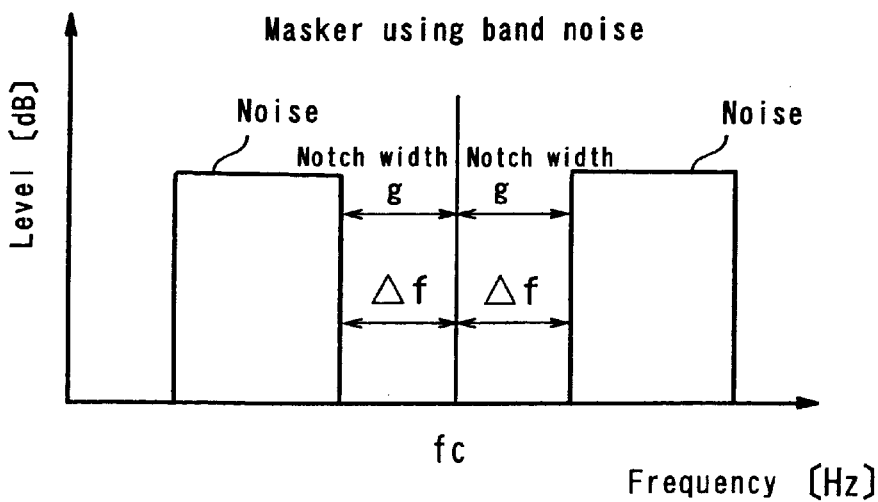

According to the embodiments of the present invention, as shown in FIG. 11(a), the masker M is provided so that the notch is added to the white noise. This masker M can however be constituted by two-band noise (high frequency side and low frequency side) as shown in FIG. 11(b).

Further, in the embodiments according to the present invention, a case where the frequency f of the tone signal output from the tone level setting element 12 agrees with the center frequency $f_c$ of the masker M output from the notch width setting element 15 (f=$f_c$) has been explained. However, it is not always necessary that these agree, but it is sufficient if the tone signal is included in the notch width.

In the embodiments according to the present invention, to find the minimum notch width (the threshold notch width) $g_{x-a}$ which can be perceived by the subject, the notch width g of the masker M is first set narrower (g=0.05) to transmit the inspection sound. When the subject cannot perceive the tone S' from the inspection sound, it has been explained that the inspection sound is transmitted again until the subject can perceive the tone S' by gradually widening the notch width g of the masker M.

However, since it is one of the objects to find the minimum notch width $g_{x-a}$ which can be perceived by the subject, the steps may be modified as follows. The notch width g of the masker M is first set wider to transmit the inspection sound to the subject in such a condition that the subject can perceive the tone S' from the inspection sound. The inspection sound is transmitted again until the subject cannot perceive the tone S' by gradually narrowing the notch width g of the masker M.

Further, in the above-mentioned embodiments according to the present invention, a case where the so-called the method of limits is used to set the level of the tone and the threshold masking level $N_x$ has been explained. However, it is possible to set these based on the phychophysical measurement method such as the two alternative forced choices for selecting either the inspection sound to which the tone is added or the inspection sound to which the tone is not added.

In the embodiments according to the present invention, a case where the method of limits is used to find the minimum notch width $g_{x-a}$ which the subject can perceive has been explained. However, again this can be found based on the psychophysical measurement method such as the two alternative forced choices.

Further, in the embodiments stated above according to the present invention, the filter shape is estimated based on the roex (p, r) filter used as a model for the auditory filter. This model function need not always be the roex (p, r) filter, but another function (e.g. roex (p) having the relationship r=0 in the roex (p, r) filter) may do if it is suitable for the auditory filter.

Since the roex (p) filter has the relationship w (g)=(1+pg) $e^{-pg}$ when the roex (p) filter is adopted as a model of the auditory filter, the formula for estimating p is identical with the formulas (3) and (4).

Also, in the above-mentioned embodiments according to the present invention, judgment is made as to whether or not the response by the subject is reasonable by delaying the transmission of the tone S' by the predetermined time t relative to the masker M at the start of transmission of the inspection sound in step SP 30 during measurement of the minimum notch width $g_{x-a}$. However, when the level of white noise is varied during measurement of the threshold masking level $N_x$ in step SP 25, it is also possible to judge the validity of the measurement of the threshold masking level $N_x$ by causing the delay of time in the tone S in the same manner.

Although there have been described what are considered to be the presently preferred embodiments of the invention,it will be understood by persons skilled in the art that variations and modifications may be made there to without departing from the gist, spirit or essence of the invention. The scope of the invention is indicated by the appended claims.

What is claimed is:

1. A method of measuring frequency selectivity comprising the steps of:

adding notched noises of predetermined notch widths to a detection sound whose frequency and sound pressure level are set to predetermined values to produce a series of different inspection sounds which are different from each other only in the value of the predetermined notch width of the notched noise added thereto;

transmitting the series of inspection sounds to a subject one at a time;

judging whether or not the subject can perceive the detection sound from each of the inspection sounds; and obtaining a threshold notch width for the subject.

2. The method of measuring frequency selectivity according to claim 1, wherein the notch width is set to a threshold notch width of normal hearing.

3. The method of measuring frequency selectivity according to claim 1, wherein the sound pressure level of the detection sound is set at a threshold of hearing of the subject or set to a sound pressure level which adds a predetermined level to said threshold of hearing.

4. The method of claim 1, wherein said judging step involves widening of said notch width.

5. The method of claim 1, wherein said judging step involves narrowing of said notch width.

6. The method of measuring frequency selectivity according to claim 1, wherein a level of said notched noise is set at a threshold masking level.

7. The method of measuring frequency selectivity according to claim 1, wherein after each of the series of different inspection sounds is produced, it is transmitted to the subject and judged whether or not the subject can perceive the detection sound from the inspection sound, prior to production of a next one of the inspection sounds.

8. A method of measuring frequency selectivity comprising the steps of:

adding noises having predetermined notch widths generated from white noise set at a threshold masking level to a detection sound whose frequency and sound pressure are set at predetermined values to produce a series of different inspection sounds which are different from each other only in the value of the predetermined notch width of the noise added thereto;

transmitting the series of inspection sounds to a subject one at a time;

judging whether or not the subject can perceive the detection sound from each of the inspection sounds; and obtaining a threshold notch width of the subject.

9. The method of claim 8, wherein said judging step involves widening of said notch width.

10. The method of claim 8, wherein said judging step involves narrowing of said notch width.

11. The method of measuring frequency selectivity according to claim 8, wherein the sound pressure level of the detection sound is set at a threshold of hearing of the subject or set to a sound pressure level which adds a predetermined level to said threshold of hearing.

12. The method of measuring frequency selectivity according to claim 8, wherein a level of said notched noise is set at a threshold masking level.

13. The method of measuring frequency selectivity according to claim 8, wherein after each of the series of different inspection sounds is produced, it is transmitted to the subject and judged whether or not the subject can perceive the detection sound from the inspection sound, prior to production of a next one of the inspection sounds.

14. A method of estimating a shape of an auditory filter by finding a coefficient p of a roex (p, r) filter used as a model of the shape of the auditory filter, comprising the steps of:

determining a threshold masking level $N_x$ based on a tone S which adds a given value x to a threshold of hearing T of a subject in frequency f;

generating a tone S' which deducts a given value a from the tone S;

generating a masker M of notch width g and level $N_x$ including the frequency f in a notch;

transmitting a detection sound which superposes the masker M on the tone S' to a subject;

measuring a minimum notch width $g_{x-a}$ of the subject by changing the notch width g;

calculating a coefficient p from the minimum notch width $g_{x-a}$ and a given value a; and estimating the shape of the auditory filter from the coefficient p and the given value x corresponding to a coefficient r.

15. The method of estimating the shape of an auditory filter according to claim 14, wherein the shape of the auditory filter is estimated by using the given value x as a parameter from the coefficient p calculated from the minimum notch width $g_{x-a}$ and the given value a, and the given value x corresponding to the coefficient r.

16. The method for estimating the shape of the auditory filter according to claim 15, wherein when at least one of the threshold masking level $N_x$ and the minimum notch width $g_{x-a}$ is obtained, transmission of the tone S' is started at predetermined time intervals after transmission of the masker M to the subject is started.

17. The method of estimating the shape of an auditory filter according to claim 14, wherein when at least one of the threshold masking level $N_x$ and the minimum notch width $g_{x-a}$ is obtained, transmission of the tone S' to a subject is started at predetermined time intervals after transmission of the masker M to the subject is started.

18. An apparatus for estimating a shape of an auditory filter by finding a coefficient p of a roex (p, r) filter used as a model of the shape of the auditory filter comprising:

a tone generation element for generating a tone of a predetermined frequency;

a tone level setting element for amplifying or attenuating the tone generated from the tone generation element to a predetermined level;

a noise generation element for generating noise without a notch;

a noise level setting element for amplifying or attenuating the noise generated at the noise generation element to a predetermined level;

a notch width setting element for providing a notch including frequency of the tone to the noise;

a notched noise superposing element for superposing the notched noise output from the notch width setting element on the tone output from the tone level setting element, and outputting an inspection sound based thereon;

an inspection sound transmission element for transmitting the inspection sound output from the notched noise superposition element to a subject; and an auditory filter calculation and indication element for calculating a coefficient p of a roex (p, r) filter based on the notch width at which the subject can perceive the inspection sound and indicating the filter shape from the coefficients p and r obtained.

19. Apparatus for estimating a shape of an auditory filter by finding a coefficient p of a roex (p, r) filter used as a model of the shape of the auditory filter, comprising:

means for determining a threshold masking level $N_x$ based on a tone S which adds a given value x to a threshold of hearing T of a subject in frequency f;

means for generating a tone S' which deducts a given value a from the tone S;

means for generating a masker M of notch width g and level $N_x$ including the frequency f in a notch;

means for transmitting a detection sound which superposes the masker M on the tone S' to a subject;

means for measuring a minimum notch width $g_{x-a}$ of the subject by changing the notch width g;

means for calculating a coefficient p from the minimum notch width $g_{x-a}$ and a given value a; and means for estimating the shape of the auditory filter from the coefficient p and the given value x corresponding to a coefficient r.

20. The apparatus for estimating the shape of an auditory filter according to claim 19, wherein when at least one of the threshold masking level $N_x$ and the minimum notch width $g_{x-a}$ is obtained, transmission of the tone S' to a subject is started at predetermined time intervals after transmission of the masker M to the subject is started.

* * * * *

UNITED STATES PATENT AND TRADEMARK OFFICE
CERTIFICATE OF CORRECTION

PATENT NO.    : 6,582,378 B1
DATED         : June 24, 2003
INVENTOR(S)   : Takeshi Nakaichi, Keisuke Watanuki and Shinichi Sakamoto It is certified that error appears in the above-identified patent and that said Letters Patent is hereby corrected as shown below:

Title page,
Item [30], Foreign Application Priority Data,
change "Jun. 5, 2000 (JP) .......... 2000-167265" to
-- Jun. 5, 2000 (JP) .......... 2000-167285 --.
Item [57], ABSTRACT,
Line 10, change "which superposes the masker M on the tone S' by selsctively" to
-- which superposes the masker M on the tone S' by selectively --.

Column 2,
Line 40, change "notch width, and obtaining the threshold notch width for the" to
-- notch width, and obtaining a threshold notch width for the --.
Line 54, change "a detection sound which sets frequency and sound pressure" to
-- a detection sound which sets frequency and a sound pressure --.
Line 55, change "level at a predetermined value t produce an inspection" to -- level at predetermined values to produce an inspection --.
Line 59, change "width, and obtaining the threshold notch width of the" to -- width, and obtaining a threshold notch width of the --.

Column 3,
Line 8, change "widening a notch width, and obtaining the threshold notch" to
-- widening the notch width, and obtaining a threshold notch --.
Line 11, change "of measuring frequency selectivity comprising the steps of" to -- of measuring frequency selectivity, comprising the steps of --.
Line 18, change "sound from the inspection sound by narrowing a notch" to -- sound from the inspection sound by narrowing the notch --.
Line 19, change "width, and obtaining the threshold notch width of the" to -- width, and obtaining a threshold notch width of the --.

Column 4,
Line 37, change "BRIEF DESCRIPTION THE DRAWINGS" to -- BRIEF DESCRIPTION OF THE DRAWINGS --.
Line 66, change "determined according to the present invention; and FIGS." to
-- determined according to the present invention; and --.
Line 67, change "11(*a*) and 11(*b*) are schematic diagram of a masker." to -- 11(*a*) and 11(*b*) are schematic diagrams of a masker. --.

Column 5,
Line 28, change "adding a notch with the desired notch width whose desired" to
-- adding a notch to the desired notch width whose desired --.

Column 9,
Line 65, change "provided which comprises a tone generation element 11, a" to
-- provided which comprises a tone or detection sound generation element 11, a --.

UNITED STATES PATENT AND TRADEMARK OFFICE
CERTIFICATE OF CORRECTION

PATENT NO.    : 6,582,378 B1
DATED         : June 24, 2003
INVENTOR(S)   : Takeshi Nakaichi, Keisuke Watanuki and Shinichi Sakamoto It is certified that error appears in the above-identified patent and that said Letters Patent is hereby corrected as shown below:

Column 9 (cont'd),
Line 66, change "tone level setting element 12, a noise generation element 13," to
-- tone or detection sound level setting element 12, a noise generation element 13, --.

Column 10,
Line 6, change "signal of a predetermined frequency f as a tone (pure tone)." to -- signal of a predetermined frequency f as a detection sound or tone (pure tone). --.
Line 44, change "element 15 on a tone S' output from the tone level setting" to
-- element 15 on a tone S' or detection sound output from the tone level setting --.

Column 11,
Line 21, change "the subject can should have been able to perceive it for the" to -- the subject should have been able to perceive it for the --.
Line 22, change "predetermined time is not output, it can be considered that" to
-- predetermined time, it can be considered that --.

Column 12,
Line 8, (in equation (3)), change "≈" to -- ≒ --.
Line 10, change "Base on the relationship a[dB] ≈ 10log(PS(0)/Ps(gx-a), the" to
-- Based on the relationship a[dB] ≒ 10log(PS(0)/Ps($g_{x-a}$)), the --.
Line 14, (in equation (4)), change "≈" to -- ≒ --.
Line 21, change "coefficient r at, for example, 10, 20, 30, 40, and 50 [dB]" to
-- coefficient r at, for example, 10, 20, 30, 40 and 50 [db] --.
Line 62, change "transmitted to the subject it is possible to set the initial level" to
-- transmitted to the subject, it is possible to set the initial level --.

Column 13,
Line 27, change "subject can perceive the Tone S' before the tone S' is" to -- subject can perceive the tone S' before the tone S' is --.
Line 30, change "transmission, of the tone S' is stopped, the response by the" to
-- transmission of the S' is stopped, the response by the --.
Line 31, change "subject is considered abnormal unstable. In this case, the" to -- subject is considered abnormal or unstable. In this case, the --.

Column 14,
Line 16, change "to the present invention, a case where the so-called the" to -- to the present invention, a case where the so-called --.
Line 19, change "is possible to set these based on the phychophysical mea-" to -- is possible to set these based on the psychophysical mea- --.
Line 26, change "explained. However, again this can be found based on the" to
-- explained. However, again, this can be found based on the --.
Line 33, change "another function (e.g. roex(p) having the relationship r = 0 in" to
-- another function (e.g., roex(p) having the relationship r = 0 in --.

UNITED STATES PATENT AND TRADEMARK OFFICE
CERTIFICATE OF CORRECTION

PATENT NO.    : 6,582,378 B1
DATED         : June 24, 2003
INVENTOR(S)   : Takeshi Nakaichi, Keisuke Watanuki and Shinichi Sakamoto It is certified that error appears in the above-identified patent and that said Letters Patent is hereby corrected as shown below:

<u>Column 14 (cont'd),</u>
Line 55, change "tions and modifications may be made there to without" to -- tions and modifications may be made thereto without --.

Signed and Sealed this

Ninth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,582,378 B1
APPLICATION NO. : 09/671439
DATED : June 24, 2003
INVENTOR(S) : Takeshi Nakaichi, Keisuke Watanuki and Shinichi Sakamoto It is certified that error appears in the above-identified patent and that said Letters Patent is hereby corrected as shown below:

Title page,
Item [30], Foreign Application Priority Data,
change "Jun. 5, 2000 (JP) ………. 2000-167265" to
-- Jun. 5, 2000 (JP) ………. 2000-167285 --.
Item [57], ABSTRACT,
Line 10, change "which superposes the masker M on the tone S' by selsctively" to
-- which superposes the masker M on the tone S' by selectively --.

Column 2,
Line 40, change "notch width, and obtaining the threshold notch width for the" to
-- notch width, and obtaining a threshold notch width for the --.
Line 54, change "a detection sound which sets frequency and sound pressure" to
-- a detection sound which sets frequency and a sound pressure --.
Line 55, change "level at a predetermined value to produce an inspection" to -- level at predetermined values to produce an inspection --.
Line 59, change "width, and obtaining the threshold notch width of the" to -- width, and obtaining a threshold notch width of the --.

Column 3,
Line 8, change "widening a notch width, and obtaining the threshold notch" to
-- widening the notch width, and obtaining a threshold notch --.
Line 11, change "of measuring frequency selectivity comprising the steps of" to -- of measuring frequency selectivity, comprising the steps of --.
Line 18, change "sound from the inspection sound by narrowing a notch" to -- sound from the inspection sound by narrowing the notch --.
Line 19, change "width, and obtaining the threshold notch width of the" to -- width, and obtaining a threshold notch width of the --.

Column 4,
Line 37, change "BRIEF DESCRIPTION THE DRAWINGS" to -- BRIEF DESCRIPTION OF THE DRAWINGS --.
Line 66, change "determined according to the present invention; and FIGS." to
-- determined according to the present invention; and --.
Line 67, change "11(*a*) and 11(*b*) are schematic diagram of a masker." to -- 11(*a*) and 11(*b*) are schematic diagrams of a masker. --.

Column 5,
Line 28, change "adding a notch with the desired notch width whose desired" to
-- adding a notch to the desired notch width whose desired --.

UNITED STATES PATENT AND TRADEMARK OFFICE
CERTIFICATE OF CORRECTION

PATENT NO.       : 6,582,378 B1
APPLICATION NO.  : 09/671439
DATED            : June 24, 2003
INVENTOR(S)      : Takeshi Nakaichi, Keisuke Watanuki and Shinichi Sakamoto It is certified that error appears in the above-identified patent and that said Letters Patent is hereby corrected as shown below:

Column 9,
Line 65, change "provided which comprises a tone generation element 11, a" to
-- provided which comprises a tone or detection sound generation clement 11, a --.
Line 66, change "tone level setting element 12, a noise generation element 13," to
-- tone or detection sound level setting element 12, a noise generation element 13, --.

Column 10,
Line 6, change "signal of a predetermined frequency f as a tone (pure tone)." to -- signal of a predetermined frequency f as a detection sound or tone (pure tone). --.
Line 44, change "element 15 on a tone S' output from the tone level setting" to
-- element 15 on a tone S' or detection sound output from the tone level setting --.

Column 11,
Line 21, change "the subject can should have been able to perceive it for the" to -- the subject should have been able to perceive it for the --.
Line 22, change "predetermined time is not output, it can be considered that" to
-- predetermined time, it can be considered that --.

Column 12,
Line 8, (in equation (3)), change "≈" to -- ≑ --.
Line 10, change "Base on the relationship a[dB]≈10log(PS(0)/Ps(gx-a), the" to
-- Based on the relationship a[dB] ≑ 10log(PS(0)/Ps($g_{x-a}$)), the --.
Line 14, (in equation (4)), change "≈" to -- ≑ --.
Line 21, change "coefficient r at, for example, 10, 20, 30, 40, and 50 [dB]" to
-- coefficient r at, for example, 10, 20, 30, 40 and 50 [db] --.
Line 62, change "transmitted to the subject it is possible to set the initial level" to
-- transmitted to the subject, it is possible to set the initial level --.

Column 13,
Line 27, change "subject can perceive the Tone S' before the tone S' is" to -- subject can perceive the tone S' before the tone S' is --.
Line 30, change "transmission, of the tone S' is stopped, the response by the" to
-- transmission of the tone S' is stopped, the response by the --.
Line 31, change "subject is considered abnormal unstable. In this case, the" to -- subject is considered abnormal or unstable. In this case, the --.

UNITED STATES PATENT AND TRADEMARK OFFICE
CERTIFICATE OF CORRECTION

PATENT NO.        : 6,582,378 B1
APPLICATION NO. : 09/671439
DATED             : June 24, 2003
INVENTOR(S)       : Takeshi Nakaichi, Keisuke Watanuki and Shinichi Sakamoto It is certified that error appears in the above-identified patent and that said Letters Patent is hereby corrected as shown below:

Column 14,
Line 16, change "to the present invention, a case where the so-called the" to -- to the present invention, a case where the so-called --.
Line 19, change "is possible to set these based on the phychophysical mea-" to -- is possible to set these based on the psychophysical mea- --.
Line 26, change "explained. However, again this can be found based on the" to -- explained. However, again, this can be found based on the --.
Line 33, change "another function (e.g. roex(p) having the relationship r = 0 in" to -- another function (e.g., roex(p) having the relationship r = 0 in --.
Line 55, change "tions and modifications may be made there to without" to -- tions and modifications may be made thereto without --.

This certificate supersedes Certificate of Correction issued December 9, 2003.

Signed and Sealed this

Nineteenth Day of September, 2006

JON W. DUDAS
*Director of the United States Patent and Trademark Office*